US006635277B2

(12) United States Patent
Sharma et al.

(10) Patent No.: US 6,635,277 B2
(45) Date of Patent: Oct. 21, 2003

(54) COMPOSITION FOR PULSATILE DELIVERY OF DILTIAZEM AND PROCESS OF MANUFACTURE

(75) Inventors: Vinay K. Sharma, Long Valley, NJ (US); Javed Hussain, Maharashtra (IN); Habil F. Khorakiwala, Mumbai (IN)

(73) Assignee: Wockhardt Limited (IN)

( * ) Notice: Subject to any disclaimer, the term of this patent is extended or adjusted under 35 U.S.C. 154(b) by 71 days.

(21) Appl. No.: 09/834,045

(22) Filed: Apr. 12, 2001

(65) Prior Publication Data

US 2003/0003149 A1 Jan. 2, 2003

Related U.S. Application Data

(60) Provisional application No. 60/287,566, filed on Apr. 12, 2000.

(51) Int. Cl.[7] ............................. A61K 9/16; A61K 9/52; A61K 9/54; A61K 9/58; A61K 9/62
(52) U.S. Cl. ..................... 424/458; 424/457; 424/461; 424/462; 424/494; 424/497
(58) Field of Search .............................. 424/497, 457, 424/458, 459, 494, 451, 461, 462, 490

(56) References Cited

U.S. PATENT DOCUMENTS

| 3,835,221 A | 9/1974 | Fulberth et al. ............... 424/20 |
| 4,369,172 A | 1/1983 | Schor et al. ................... 424/19 |
| 4,374,829 A | 2/1983 | Harris et al. ................. 424/177 |

(List continued on next page.)

FOREIGN PATENT DOCUMENTS

| EP | 0324981 | 7/1989 |
| EP | 0527637 | 2/1993 |

OTHER PUBLICATIONS

Knop, K., et al., "Influence of surfactants of different charge and concentration on drug release from pellets coated with an aqueous dispersion of quaternary acrylic polymers", *S.T.P. Pharma Sciences*, 796, pp. 505–512, (1997).

Lehman, K.O., "Chapter 4: Chemistry and Application Properties of Polymethacrylate Coating Systems", *In: Aqueous Polymeric Coatings for Pharmaceutical Dosage Forms*, Second Edition, James W. McGinty, Ed., Marcel Dekker, Inc., pp. 101–176, (1997).

Narisawa, S., et al., "An organic acid induced sigmoidal release for oral controlled release preparations", *Pharm. Res.*, 11, pp. 111–116, (1994).

*Primary Examiner*—James M. Spear
(74) *Attorney, Agent, or Firm*—Schwegman, Lundberg, Woessner & Kluth, P.A.

(57) ABSTRACT

A once-a-day controlled release drug delivery system of diltiazem hydrochloride is provided, which is bioequivalent in plasma profile of Cardizem CD. The fast, medium, and slow release fractions are prepared using various compositions and weight gains. The individual fill weights are computed and then are filled into the same capsule using specialized encapsulation equipment using a triple-filling process. A preferred membrane dispersion that is used for preparing the fast release fraction contains 0.2% of sodium lauryl sulfate along with 20% of water soluble plasticizer (triethyl citrate), and 2% silicone dioxide, based on quaternary polymethacrylate on the weight basis. This combination provides an initial pulsatile burst after a lag time of 2 hours, leading to in-vivo bioequivalence. The preferred membrane dispersion that is used for preparing the medium release and the slow release fractions contain 16% of water soluble plasticizer along with 5% silicone dioxide, based on quaternary polymethacrylate. This combination provides an optimal glass transition temperature that allows for the preparation of exceptionally increased weight gains. Additionally, it provides targeted input of drug release for achieving bioequivalence. Regardless of significant in-vitro inequivalence to the release rate profile of the innovator product, the in vivo-equivalence data comply with required regulatory guidelines.

21 Claims, 5 Drawing Sheets

U.S. PATENT DOCUMENTS

| | | | |
|---|---|---|---|
| 4,416,819 A | 11/1983 | Nagao et al. | 260/292.3 B |
| 4,438,035 A | 3/1984 | Gaino et al. | 260/239.3 B |
| 4,472,380 A | 9/1984 | Harris et al. | 424/177 |
| 4,610,870 A | 9/1986 | Jain et al. | 424/19 |
| 4,721,619 A | 1/1988 | Panoz et al. | 424/459 |
| 4,801,460 A | 1/1989 | Goertz et al. | 424/465 |
| 4,808,413 A | 2/1989 | Joshi et al. | 424/458 |
| 4,828,840 A | 5/1989 | Sakamoto et al. | 424/474 |
| 4,834,965 A | 5/1989 | Martani et al. | 424/488 |
| 4,834,985 A | 5/1989 | Elger et al. | 424/488 |
| 4,839,177 A | 6/1989 | Colombo et al. | 424/482 |
| 4,871,731 A | 10/1989 | Walker | 514/211 |
| 4,879,289 A | 11/1989 | Zobrist et al. | 514/211 |
| 4,880,631 A | 11/1989 | Haslam et al. | 424/424 |
| 4,886,668 A | 12/1989 | Haslam et al. | 424/424 |
| 4,891,230 A | 1/1990 | Geoghegan et al. | 424/461 |
| 4,894,240 A | 1/1990 | Geoghegan et al. | 424/497 |
| 4,904,476 A | 2/1990 | Mehta et al. | 424/456 |
| 4,917,899 A | 4/1990 | Geoghegan et al. | 424/461 |
| 4,960,596 A | 10/1990 | Debregeas et al. | 424/458 |
| 4,963,365 A | 10/1990 | Samejima et al. | 424/46 L |
| 4,963,545 A | 10/1990 | Zobrist et al. | 514/211 |
| 4,968,507 A | 11/1990 | Zentner et al. | 424/465 |
| 4,983,598 A | 1/1991 | Cavero et al. | 514/211 |
| 4,992,277 A | 2/1991 | Sangekar et al. | 424/465 |
| 4,999,189 A | 3/1991 | Kogan et al. | 424/79 |
| 5,000,962 A | 3/1991 | Sangekar et al. | 424/482 |
| 5,002,776 A | 3/1991 | Geoghegan et al. | 424/497 |
| 5,026,560 A | 6/1991 | Makino et al. | 424/494 |
| 5,068,112 A | 11/1991 | Samejima et al. | 424/495 |
| 5,112,621 A | 5/1992 | Stevens et al. | 424/497 |
| 5,133,974 A | 7/1992 | Paradissis et al. | 424/480 |
| 5,137,733 A | 8/1992 | Noda et al. | 424/497 |
| 5,149,542 A | 9/1992 | Valducci | 424/493 |
| 5,202,128 A | 4/1993 | Morella et al. | 424/469 |
| 5,213,811 A | 5/1993 | Frisbee et al. | 424/493 |
| 5,219,621 A | 6/1993 | Geoghegan et al. | 424/462 |
| 5,225,202 A | 7/1993 | Hodges et al. | 424/480 |
| 5,229,131 A | 7/1993 | Amidon et al. | 424/451 |
| 5,229,135 A | 7/1993 | Philippon et al. | 424/494 |
| 5,252,337 A | 10/1993 | Powell | 424/456 |
| 5,254,347 A | 10/1993 | Samejima et al. | 424/495 |
| 5,260,068 A | 11/1993 | Chen | 424/451 |
| 5,273,760 A | 12/1993 | Oshlack et al. | 424/480 |
| 5,286,497 A | 2/1994 | Hendrickson et al. | 424/490 |
| 5,288,505 A | 2/1994 | Deboeck et al. | 424/497 |
| 5,310,558 A | 5/1994 | Pozzi et al. | 424/476 |
| 5,320,853 A | 6/1994 | Noda et al. | 424/472 |
| 5,336,504 A | 8/1994 | Geoghegan et al. | 424/462 |
| 5,376,384 A | 12/1994 | Eichel et al. | 424/480 |
| 5,458,888 A | 10/1995 | Chen | 424/464 |
| 5,470,584 A | 11/1995 | Hendrickson et al. | 424/490 |
| 5,472,712 A | 12/1995 | Oshlack et al. | 424/480 |
| 5,496,561 A | 3/1996 | Okada et al. | 424/480 |
| 5,508,040 A | 4/1996 | Chen | 424/451 |
| 5,529,790 A | 6/1996 | Eichel et al. | 424/480 |
| 5,529,791 A | 6/1996 | Deboeck et al. | 424/480 |
| 5,567,441 A | 10/1996 | Chen | 424/494 |
| 5,578,321 A | 11/1996 | Sherman | 424/453 |
| 5,582,837 A | 12/1996 | Shell | 424/451 |
| 5,582,838 A | 12/1996 | Rork et al. | 424/472 |
| 5,601,845 A | 2/1997 | Buxton et al. | 424/495 |
| 5,614,220 A | 3/1997 | Hirakawa et al. | 424/480 |
| 5,616,345 A | 4/1997 | Geoghegan et al. | 424/497 |
| 5,622,716 A | 4/1997 | Barth | 424/461 |
| 5,629,017 A | 5/1997 | Pozzi et al. | 424/476 |
| 5,645,858 A | 7/1997 | Kotwal et al. | 424/495 |
| 5,670,172 A | 9/1997 | Buxton et al. | 424/495 |
| 5,683,716 A | 11/1997 | Hata et al. | 424/451 |
| RE35,903 E | 9/1998 | Debregeas et al. | 424/458 |
| 5,830,503 A | 11/1998 | Chen | 424/480 |
| 5,834,023 A | 11/1998 | Chen | 424/497 |
| 5,834,024 A | 11/1998 | Heinicke et al. | 424/497 |
| 5,840,329 A | 11/1998 | Bai | 424/458 |
| 5,879,714 A | 3/1999 | Sherman | 424/489 |
| 5,914,134 A | 6/1999 | Sharma | 424/497 |
| 5,922,352 A | 7/1999 | Chen et al. | 424/465 |
| 5,958,458 A | 9/1999 | Norling et al. | 424/490 |
| 5,968,552 A | 10/1999 | Sherman | 424/456 |
| 6,033,687 A | 3/2000 | Heinicke et al. | 424/497 |
| 6,039,979 A | 3/2000 | Gendrot et al. | 424/497 |
| 6,074,669 A | 6/2000 | Nagaprasad et al. | 424/458 |

|  | DIL-26 B | | DIL-33 B | | DIL-60 B | |
|---|---|---|---|---|---|---|
|  | % FRACTION | % WEIGHT GAIN | % FRACTION | % WEIGHT GAIN | % FRACTION | % WEIGHT GAIN |
| FRF | 43.0 | 14.0 | 37.0 | 14.0 | 37.0 | 14.0 |
| SRF1/MRF | 28.5 | 63.0 | 31.5 | 63.0 | 26.0 | 40.0 |
| SRF2 | 28.5 | 67.0 | 31.5 | 67.0 | 37.0 | 52.5 |

COMPOSITION FOR PULSATILE DELIVERY OF DILTIAZEM AND PROCESS OF MANUFACTURE

CROSS-REFERENCE TO RELATED APPLICATIONS

This application claims priority from U.S. provisional patent application Ser. No. 60/287,566, filed on filed Apr. 12, 2000, which is incorporated herein by reference.

BACKGROUND OF THE INVENTION

1. Field Of The Invention

A three-pellet, pulsatile drug delivery system results in bioequivalence to Cardizem® CD. The fast release membrane (FRF) composition includes an anionic surface active agent which assures complete drug release after providing a desired lag time. The medium release fraction (MRF) and the slow release fraction (SRF) are plasticized with decreased concentrations of triethyl citrate and increased concentrations of silicone dioxide powder for improved process performance.

2. Background Of The Art

Diltiazem is a benzothiazine derivative possessing calcium antagonist activity. Diltiazem blocks the influx of calcium ions in smooth and cardiac muscle and thus exerts potent cardiovascular effects. Diltiazem has been shown to be useful in alleviating symptoms of chronic heart disease, particularly angina pectoris and myocardial ischemia and hypertension, while displaying a low incidence of side effects. The first dosage forms of diltiazem sold in the United States were tablets containing 30 mg or 60 mg of diltiazem hydrochloride sold under the tradename Cardizem® by Marion Laboratories Inc. Single oral doses of 30 mg and to 120 mg of Cardizem® tablets result in peak plasma levels about 2 to 3 hours after ingestion, and the elimination half-life is about 3 to 5 hours. Because of the relatively rapid absorption of diltiazem hydrochloride from such tablets and rapid elimination, the usual dosage regimen for immediate release tablets is for a dose to be taken three or four times daily. The need for such frequent administration may reduce patient compliance. Thus adverse therapeutic effects can arise. It thus became apparent that it would be preferable to administer diltiazem hydrochloride in a dosage form that releases the diltiazem hydrochloride much more slowly than Cardizem® tablets, so as to enable the frequency of ingestion by the patient to be reduced to once daily.

A formulation of diltiazem hydrochloride that controls the rate of release to enable once daily administration is sold in the United States under the tradename Dilacor® XR by Rhone-Poulenc Rorer Pharmaceuticals Inc. Dilacor® XR is produced as two-piece hard gelatin capsules, with each capsule containing a plurality of tablets. The 180 mg strength of Dilacor® XR contains three tablets and the 240 mg strength contains four tablets. The same tablets are used in both capsules, and each tablet contains 60 mg of diltiazem hydrochloride.

The tablets used in Dilacor® XR are made in accordance with the invention of U.S. Pat. No. 4,839,177. Each tablet is comprised of a cylindrical core containing diltiazem hydrochloride mixed with inactive ingredients that include a polymer that swells and forms a gel upon contact with aqueous fluids. Because the gel has high viscosity, it swells and dissolves only very slowly in the gastrointestinal fluids to thereby retard the rate of release of the diltiazem hydrochloride. To further retard the release, insoluble polymeric platforms are affixed to the top and bottom of the cylindrical core, thus leaving only the periphery exposed to the gastrointestinal fluid. The formulation of Dilacor® XR capsules successfully accomplishes gradual release to enable once daily dosing, but the Dilacor® XR formulation requires complex and expensive procedures to produce. In particular, production of the tablets contained in Dilacor® XR capsules requires production of cores containing the diltiazem hydrochloride and the affixing thereto of the insoluble platforms.

Another formulation of diltiazem hydrochloride suitable for once daily administration is now sold in the United States under the trademark Cardizem® CD, by Marion Laboratories Inc. Cardizem® CD is sold as capsules containing a multitude of beads. The composition of the beads contained in Cardizem® CD capsules is described in U.S. Pat. No. 5,286,497. The beads are made using core seeds to which is applied a first coating containing the diltiazem hydrochloride. Over the first coating, further coatings of polymers are applied which serve to slow down and control the rate at which the diltiazem hydrochloride is released from the beads in gastrointestinal fluids.

As explained in U.S. Pat. No. 5,286,497, there is a particular dissolution profile found to be optimum for once daily administration. This desired dissolution profile, when measured in a type 2 dissolution apparatus according to U.S. Pharmacopoeia XXII, in 0.1 NHCL at 100 rpm is as follows:

a) from 20–45% released after 6 hours;
b) from 25–50% released after 12 hours;
c) from 35–70% released after 18 hours;
d) not less than 70% released after 24 hours;
e) not less than 85% released after 30 hours;

The invention of U.S. Pat. No. 5,286,497 achieves this dissolution profile by using a mixture of beads with two differing amounts of coating. The beads with the lesser amount of coatings are referred to as "rapid release diltiazem beads" and the beads with the greater amount of coating are referred to as "delayed release diltiazem beads". It is disclosed that by making each of these types of beads so as to comply with particular dissolution requirements, the mixture of the two types of beads produces the desired dissolution profile for the final composition.

A difficulty with the invention of U.S. Pat. No. 5,286,497 is that it is difficult to reliably make the two types of beads so as to get the required dissolution profile for the final mixture. In particular, the desired dissolution profile requires that the amount released must exceed 20% after 6 hours, but must not exceed 50% after 12 hours. This requires that the "rapid release diltiazem beads" give a sharp, step-like release of the diltiazem. Otherwise, if the amount released increases only gradually with time, beads formulated to assure that at least 20% of the diltiazem is released from the final mix after 5 hours will also cause more than 50% to be released after 10 hours, thus causing the final composition to fail to meet the defined requirements.

U.S. Pat. No. 5,968,552 discloses beads containing diltiazem hydrochloride made by processes the same as or similar to those disclosed in U.S. Pat. No. 5,286,497. However, instead of mixing only two types of beads, referred to as "rapid release beads" and "delayed release bead", three types of beads are made which will be referred to herein as "rapid release beads", "intermediate release beads", and "delayed release beads". By using an appropriate mixture of these three types of beads, with three different amounts of coating, it is possible to obtain the desired dissolution profile for the final mix, without the need for the individual types of beads to have the sharp step-like release profile required by the invention of U.S. Pat. No. 5,286,497.

The three bead combination (rapid release, intermediate release, and delayed release beads) of U.S. Pat. No. 5,968,552 will typically exhibit in vitro dissolution profiles as shown in the Patent when measured in 0.1 NHCL using a type 2 apparatus at 100 rpm according to U.S. Pharmacopoeia XXII. A typical profile (preferred profile) composition is Rapid Release at 3 hours 40–100% (70%), Intermediate Release at 6 hours 0 to 30% (17%), Delayed Release at 18 hours 30 to 60% (45%). The beads are provided in a manner so that the available diltiazem HCl from each set is approximately 18% in rapid release beads, about 20% in intermediate release beads, and 65% delayed release beads. This distribution cannot possibly provide bioequivalence to the biphasic plasma profile of Cardizem® CD. The release profile is only more similar to the release profile of Cardizem®, as compared to that of U.S. Pat. No. 5,286,497. Even 100% release of the fast release fraction in three hours could contribute a maximum of about 28% of the diltiazem HCl (18%×the 40–100% release rate of the fast release fraction plus 15%×the 0–15% release rate in the intermediate release fraction and 67×0–10% of the delayed release fraction) in three hours. This profile is asserted to provide a better dissolution profile for the final mix, without the need for individual types of beads having the sharp step-like release profile required by 5,286,497, yet still would not be expected to met the bioequivalence plasma profile of Cardizem® CD.

All three types of beads in U.S. Pat. No. 5,968,552 will usually be made by taking the same cores containing diltiazem hydrochloride and applying different amounts of polymeric coating to slow down the release. The intermediate release beads will typically have more coating than the rapid release beads, and similarly the delayed released beads will typically have more coating than the intermediate release beads. It follows that the intermediate release beads will contain a smaller percent diltiazem hydrochloride by weight than the prompt release beads, and similarly the delayed release beads will contain a smaller percent diltiazem hydrochloride by weight than the intermediate release beads. The final blend of beads will typically contain about 15% by weight rapid release beads, about 20% by weight intermediate release beads and about 65% by weight delayed released beads.

In view of the differences in percent diltiazem hydrochloride content as aforesaid, it follows that in the final blend, about 18% of the diltiazem hydrochloride content will be in the rapid release beads, about 20% in the intermediate release beads, and about 62% in the delayed release beads. By taking into account these percentages along with the typical dissolution data of the beads, the dissolution at 6 hours will be about 27%, and at 12 hours will be about 44%.

U.S. Pat. No. 5,914,134 describes Applicant's pulsatile technology for diltiazem hydrochloride. This technology is based on drug layering of diltiazem hydrochloride in a suspension form on NuPareils® (sugar spheres, 30/35 mesh). Thereafter, the drug-layered pellets are precisely divided into three fractions for subsequent application of multiple membrane coats. Depending on the number of membrane coats applied, the delivery system is designed to deliver about 40% of the total dose in a pulsatile, site-specific manner, in the proximal segment of the small intestine and about 60% of the total dose in a sigmoidal, site-specific manner in the distal segment of the small intestine and the large intestine. The drug delivery pellet unit hydrates by controlled diffusion of water into the membrane coated, drug layered pellet. The water-soluble, porosity controlling plasticizer in the membrane coat dissolves and creates water-filled aqueous channels through which the drug permeates towards a specific segment of the digestive tract.

The plasticizer triethylcitrate in the polymeric membrane of U.S. Pat. No. 5,914,134 is responsible for driving the drug in the form of a pulse in solution form whereas the number and thickness of the membrane coatings dictate the precise time of drug delivery. The drug delivery system releases the drug from each of the three fractions in less than three hours from the beginning of drug release. It was observed that this formulation presented an apparent in-vitro insufficiency in drug release in pH 6.8 phosphate buffer. Furthermore, the innovator's product, Cardizem® CD, is pH-independent.

The polymers poly(EA-MMA-TAMCl) 1:2:0.1 and 1:2:0.2 form films that are water-insoluble, and their permeability, which is independent of pH, depends on the content of quaternary ammonium groups. It is high when the TAMCl (trimethyl ammonium chloride) proportion is high. Aqueous dispersions of these polymers contain latex-like particles. The MFT (minimum film formation temperature) of the pure dispersions are around 40 and 50° C. Addition of 10–20% plasticizer is necessary to reduce the MFT to below 20° C. The addition of plasticizer is important to increase the flexibility of the films but also to lower the MFT which facilitates coating process. MFT of RS 30D value with 20% plasticizer is 5° C. (Refer to Klaus O. R. Lehmann, Chapter 4,"Chemistry and Application Properties of Polymethacrylate Coating Systems", In: Aqueous Polymeric Coatings for Pharmaceutical Dosage Forms, Second Edition, Edited by James W. McGnity, Marcel Dekker, Inc., pp. 101–176). These authors state "Addition of 20% plasticizer results in a considerable increase in the elongation of break whereas tensile strength at break is lowered, so that optimum film properties will be found in between".

Triethyl citrate decreases the glass transition temperature of quaternary polymethacrylate. It must be used in conjunction with an antiadherant such as silicone dioxide (Syloid® 244 FP) to prevent the agglomeration of quaternary polymethacrylate-coated pellets. The agglomeration problem is related to a decrease in the glass transition temperature (Tg) of quaternary polymethacrylate. It is reported in literature that the films of quaternary polymethacrylate are not sufficiently flexible. Even with 10% plasticizer they show some brittleness. Furthermore, a 20% plasticizer results in considerable increase in the elongation of break, whereas tensile strength at break is lowered. Therefore, the optimum film properties are found in between the two concentrations (10% and 20%) of the plasticizer.

To assure completeness of drug release (indicating bioequivalence of $C_{max}$) from the fast release fraction, sodium lauryl sulfate, an anionic surfactant with $pK_a$ of 1.9 was included in the polymeric membrane. "The addition of anionic surface active agents such as sodium lauryl sulfate and sodium taurocholate to the dissolution medium (phosphate buffer at pH 6.8) led to modified release behavior when pellets coated with quaternary polymethacrylate was tested. The chloride anions of the quaternary ammonium groups of the polymer were exchanged by the more lipophilic surfactant anions (lauryl sulfate, taurocholate)." K. Knop and K. Matthee, Influence of surfactants of different charge and concentration on drug release from pellets coated with an aqueous dispersion of quaternary acrylic polymers, S.T.P PHARMA SCIENCES, 796) 507–512 91997). Sodium lauryl sulfate is surface active only in the ionized state. It is only 10% ionized in 0.1N HCl. However, it still acts as an effective membrane modifier when the product developed under the current invention was tested for drug release in 0.1N HCl, which is an unexpected finding.

Other inventors observed in-vitro insufficiency in the release of diltiazem hydrochloride from polymeric membranes comprised of polymethacrylate cations, plasticizers, and antiaderants. In order to resolve this problem, a pH-independent drug delivery system of diltiazem hydrochloride was developed by adding dicarboxylic acids such as fumaric acid in the drug-loaded beads, followed by coating with plasticized polymethacrylate membrane (Eudragit® RS 30D, plasticized with water-insoluble acetyl tributyl citrate). The polymeric membrane controls drug release by hydration/swelling of the membrane, possibly due to a polymethacrylate cation-fumarate anion interaction. Narisawa, S. et al., An Organic Acid Induced Sigmoidal Release For Oral Controlled Release Preparations. Pharm. Res., Vol 11, 111–116 (1994). These authors established a relationship between $t_{50, hours}$ (time for 50% of drug released) and the $pK_a$ of the organic acid and concluded that the optimum range for the $pK_a$ values for achieving near-pulsatile (sigmoidal) release for slightly soluble drugs is between 4–5.

A number of U.S. Patents disclose once-daily oral delivery formulations of diltiazem hydrochloride. U.S. Pat. No. 5,439,689 is assigned to Carderm Capital L. P. This patent discloses a once-a-day oral formulation of diltiazem hydrochloride having a stair stepped release profile generated by two populations of diltiazem beads which release the drug at two different intervals of time, 3–9 hours following lag times of 3 hours and 15–21 hours following a lag time of 15 hours. Although such a formulation releases diltiazem hydrochloride over 24 hours, it relies heavily on the drug release based on organic acids, which are an irritant to the mucosa.

U.S. Pat. No. 5,529,791 is assigned to Galephar P. R., Inc., Ltd. This invention is based on a central core prepared with diltiazem salt and a wetting agent in admixture with the diltiazem salt. A central core is subsequently coated with a microporous membrane comprising at least a water-soluble or water-dispersible polymer or copolymer, and a water-, acid- and base-insoluble polymer and a pharmaceutically-acceptable adjuvant. It is apparent that this invention has not considered the absorption physiology and first-pass intestinal metabolism of diltiazem in its design.

U.S. Pat. No. 5,834,024 (assigned to F. H. Faulding and Co., Ltd.) discloses a controlled absorption diltiazem pellet formulation for oral administration comprises a core having diltiazem or a pharmaceutically acceptable salt thereof as the active ingredient. The core is surrounded by a coating having only a single layer. That layer comprises a relatively major proportion of talc and relatively minor proportion of sodium lauryl sulfate admixed with a minor proportion of a pharmaceutically acceptable, film-forming, first polymer permeable to water and diltiazem, and a major proportion of a pharmaceutically acceptable film-forming, second polymer that is less permeable to water and diltiazem than the first polymer. The core and the coating layer both exclude organic acids. The composition of the coating layer as well as the proportion of core to coating layer are effective to permit release of the diltiazem allowing controlled absorption following oral administration. By combining short lag and long lag pellets into a single formulation, the release of diltiazem is controlled over a twenty four hour period.

U.S. Pat. No. 5,834,023 (Andrx Pharmaceuticals Inc.) describes a once-a-day controlled release diltiazem formulation which includes: (a) from 20 to 50% by weight of enteric polymeric membrane coated pellets comprising a polymer membrane coated core which comprises a biologically inert core which is coated with a first layer which consists essentially of diltiazem and a polymeric binder; and a second layer which comprises a membrane comprising a pH dependent polymeric material; and (b) from 50% to 80% by weight of delayed pulse polymeric membrane coated pellets comprising a polymeric membrane coated core which comprises a biologically inert core which is coated with a first layer which consists essentially of diltiazem and a polymeric binder and a second layer which comprises a polymeric membrane which will substantially maintain its integrity in the varying pH conditions of the gastrointestinal tract but is permeable to diltiazem; and (c) a unit dose containment system.

U.S. Pat. No. 5,567,441 assigned to Andrx Pharmaceuticals, Inc., describes unit dosage forms of diltiazem hydrochloride which comprise a two fraction system, enteric polymeric membrane coated pellets and delayed pulse polymeric membrane coated pellets. This invention relies on the biological system for subject-to-subject and within subject reliability of gastrointestinal movement of enteric-coated pellets and dissolution of the complete enteric coat for bio-response in the initial phase.

Cardizem® CD is described as a once-a-day extended release capsule containing diltiazem and fumaric acid. The file history of U.S. Pat. No. 5,286,497 is believed to indicate that the formulation disclosed in that patent is the formulation for Cardizem® CD. Furthermore, the formulation for Cardizem® CD is identified in the file history of U.S. Pat. No. 5,286,497 as having a "stair-step release profile" which has a rapid release bead and an extended release bead.

SUMMARY OF THE INVENTION

A three-pellet, quaternary polymethacrylate-based drug delivery system results in a system with bioequivalence to Cardizem® CD. A fast release fraction (FRF) composition displays a novel release profile from previous compositions, yet provides a very strong match with Bioequivalent Plasma profiles of Cardizem® CD, the Fast Release Fraction including an anionic surface active agent which assures complete drug release after providing a desired lag time. A medium release fraction (MRF) and a slow release fraction (SRF) are plasticized with decreased concentrations of triethyl citrate and increased concentrations of silicone dioxide powder for improved process performance.

A drug-layered pellet is comprised of diltiazem and a binder (e.g., less than 0.1% by weight of the binder, preferably less than 0.05%, or less than 0.01% by weight of the binder). A three-pellet, quaternary polymethacrylate-based drug delivery system is composed of a fast release fraction (FRF), a medium release fraction (MRF) and a slow release fraction (SRF). The preferred proportion of these fractions is 35–40FRF/24–28MRF/35–40SRF (e.g., 37/26/37). The preferred weight gain of these fractions is 11–17% (12–15%, 13%), 33–45% (36–39%, 37%), and 45–52% (e.g., 48–50%, 49%) with respect to the coatings. The fast release membrane composition includes an anionic surface-active agent such as sodium lauryl sulfate. A hydrophilization of the fast release fraction (FRF) creates a microporous structure, assuring total drug release delivered as a pulse (referred to as pulsatile delivery). In the absence of such a release profile for the FRF, the product is not believed to provide a bioequivalent plasma release profile compared to that of Cardizem(® CD.

The medium release fraction (MRF) and the slow release fraction (SRF) may be plasticized with suitable concentrations of plasticizer such as triethyl citrate for optimum film coating performance. Several studies were conducted prior to arriving at this conclusion. When the triethyl citrate concentration was 20%, a talc concentration of 20% and a Syloid® concentration of 2% (based on dry quaternary polymethacrylate weight), the fluidization patterns could not be optimized with changing fluidization plates, partition heights, and optimized spray patterns by changing nozzle positions and apertures. A decrease of triethyl citrate to 16% (e.g., 14–18% or 15–17%) and a simultaneous increase of Syloid® to 5% (e.g., 3.5–6.5% or 4–6%, based on dry quaternary polymethacrylate weight) resulted in a highly efficient, reproducible, and scalable film coating operation.

DETAILED DESCRIPTION OF THE INVENTION

Figure 1:
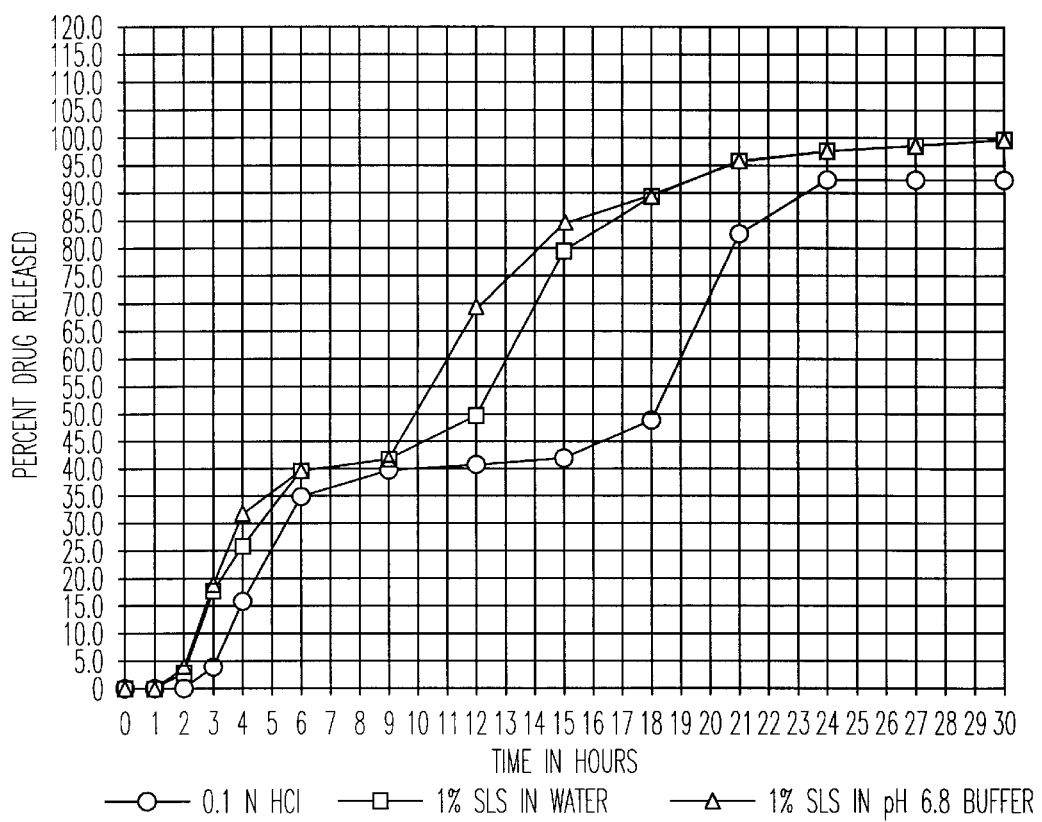
FIG. 1 shows drug release profiles for applicant's formulation (U.S. Pat. No. 5,914,134) in 1% sodium lauryl sulfate in pH 6.8 phosphate buffer and other media.
Figure 2:
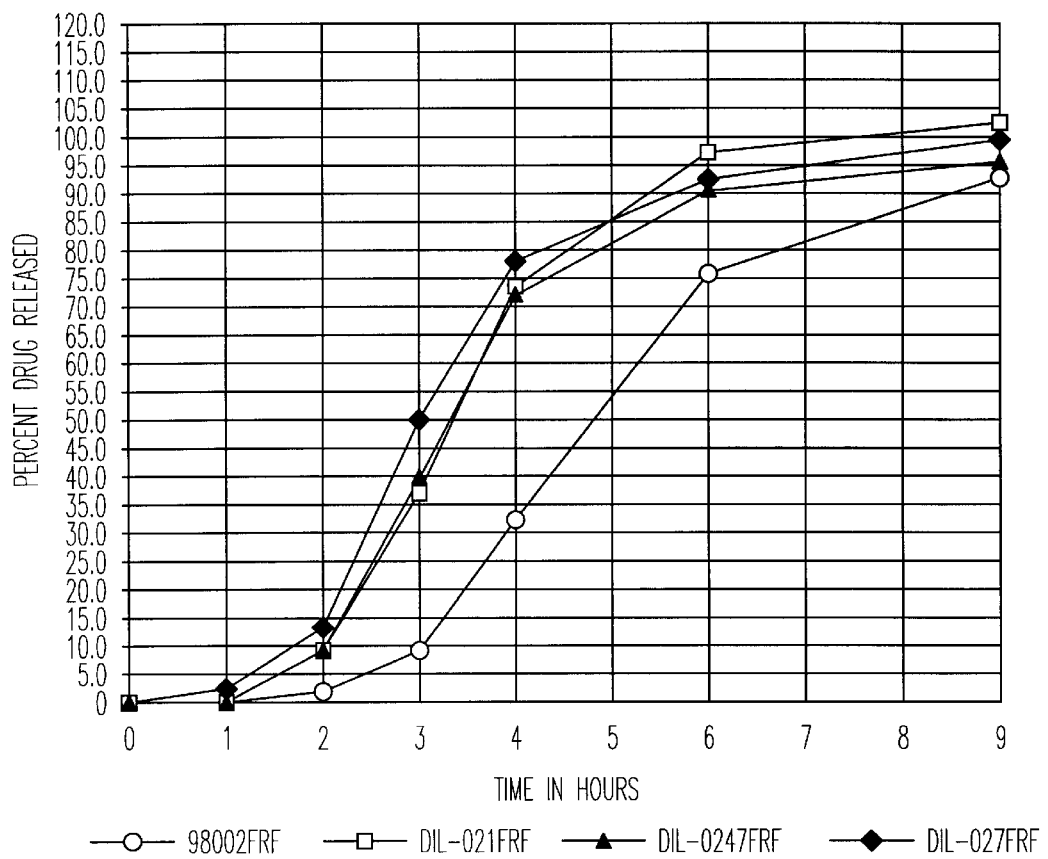
FIG. 2 shows comparisons of fast release fractions containing 0.1 (DIL-021FRF), 0.2 (DIL-024FRF) and 0.3 (DIL-027FRF) of sodium lauryl sulfate based on cumulative percent released for several formulations containing sodium lauryl sulfate based on total solids in a fast release fraction (FRF).
Figure 3:
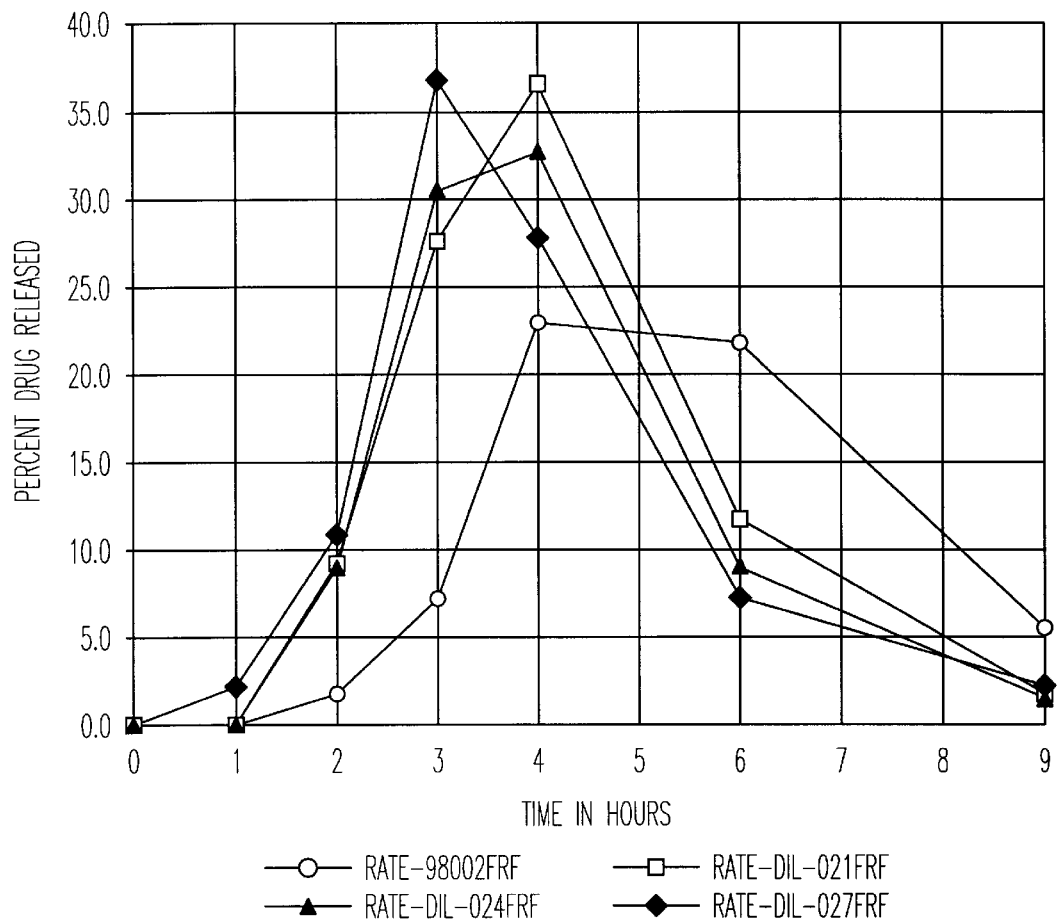
FIG. 3 shows the comparison of rates of drug release for the data in FIG. 2.
Figure 4:
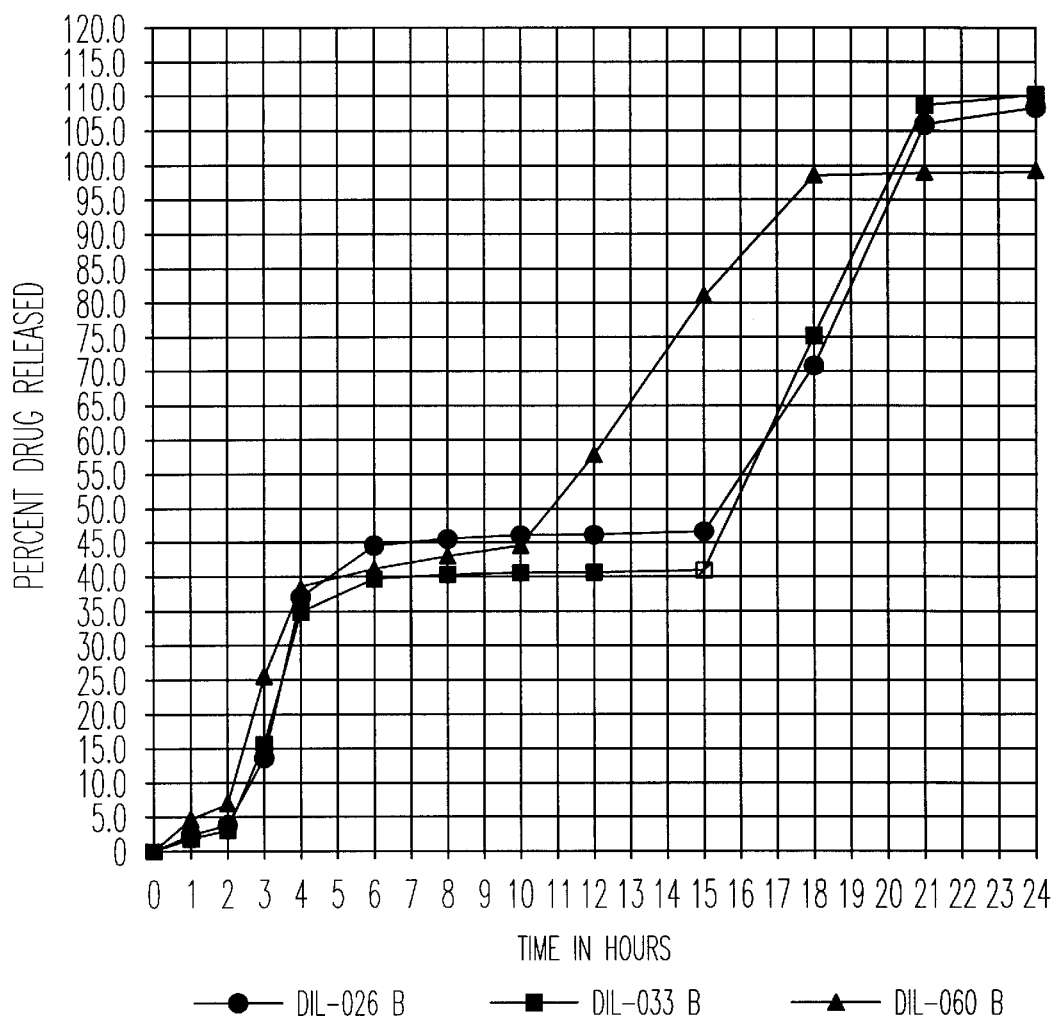
FIG. 4 shows the influence of including sodium lauryl sulfate (0.1% of the weight of the pellet) in the fast release fraction membrane of a U.S. Pat. No. 5,914,134-based formulation on in-vitro performance and varying drug inputs for the fast release fraction, medium release fraction and slow release fraction as presented in the Table above FIG. 4.

The present drug delivery system is a site-specific dosage form. The term pulsatile is used to describe the rapid delivery of a dose of the drug ($d_1, d_2, \ldots d_n$) into the portal system over a specific time interval ($\Delta_{t1}, \Delta_{t2} \ldots \Delta_{tn}$) respectively preceded by lag times of ($t_{lag1}, t_{lag2} \ldots t_{lagn}$). This regimen is equivalent to the rate of drug release from immediate release dosage forms. The shape of pulsatile rate of drug delivery is characterized by a Gaussian distribution.

The drug-layered pellets are prepared, for example, by slowly dispensing scoops of powdered diltiazem hydrochloride in a dispersion of hydroxypropylmethyl cellulose (e.g., traded as Opadry® Clear Y-5-7095 by Colorcon, U.S.A.) in water, mixing initially at fast speed, followed by slow-speed, continued mixing. The criteria of good mixing is met when the drug dispersion meets the required assay (36% w/w) and the assay uniformity specifications when sampled at various heights in the mixing container.

Next, the pump equipped with a specific tubing (Watson Marlow, peristaltic pump) is calibrated. A calibration plot of liquid delivery rate (g/min) as a function of pump rate is prepared.

A specific distribution of non-pareils (traded as NuPareils®), ranging from about 30/35 mesh to 40/45 mesh is charged into GPCG-5, 7 inch (17.8 cm) Wurster HS. The product container is configured as follows: up-bed G plate, down-bed B plate, nozzle port 1.2 mm, atomizing air 3.0 bar, angle flush, filter shake 3/30 (for 3 seconds per 30 seconds), product screen 100 mesh dutchweave, and starting partition height 20 mm. Using appropriate air volume, inlet temperature and spray rate, the required amount of drug dispersion is applied to the NuPareils®. A sub-coat dispersion of 10% w/w of Opadry® Clear YS-3-7065 is applied on the drug-layered pellets to add on a dry weight gain of 1%. Next, the drug-layered pellets are divided into 43/28.5/28.5 or 37/31.5/31.5 distributions, preferably 37/26/37. The drug-layered pellets are 82 percent retained on −16/+18 and 18% on −18/+20 mesh.

The system may also be described as a once-a-day controlled release drug delivery system of diltiazem hydrochloride comprising a blend of pellet fractions:

A) a fast release fraction of diltiazem HCl having multiple layers of diltiazem HCl particles on a drug bead substrate and a membrane coating dispersion over the multiple layers with a first weight gain, the fast release fraction providing a profile of drug release of greater than 10% Total Drug Released in 3 hours and less than 40% Total Drug Released in 3 hours;

B) a medium release fraction of diltiazem HCl multiple layers of diltiazem HCl particles on a drug bead substrate and a membrane coating dispersion over the multiple layers with a second weight gain; and C) a slow release fraction of diltiazem HCl having multiple layers of diltiazem HCl particles on a drug bead substrate and a membrane coating dispersion over the multiple layers with a third weight gain;

the blend of pellets exhibiting the following cumulative in-vitro drug release profile when tested in the USP Dissolution Apparatus, Type II, in 0.1N HCl maintained at 37° C., using 100 RPM:

a) 20–40% released in 6 hours b) 55–70% released in 12 hours, and c) 75–100% (e.g., equal to or more than 75%) released in 18 hours.

The beads in the drug delivery system may comprise diltiazem hydrochloride deposited as multilayers of an aqueous dispersion of diltiazem hydrochloride in low viscosity hydroxypropyl methyl cellulose. The multilayers are formed by the stacking of beads over the seed provided at the beginning of the process. The three drug bead substrates may be divided into three multilayer beads of weight percentages of diltiazem hydrochloride comprising 35–43%/24–32%/28–40 or 37–43%/26–31.5%/28.5–37%. The drug may, for example only, have the membrane coating on the drug bead substrate of the fast release fraction (FRF) comprise a weight gain of from 10–20%; the membrane coating on the drug bead substrate of the fast release fraction (FRF) comprise a weight gain of from 13–15%; and the membrane coating on the drug bead substrate of the fast release fraction (FRF) comprise a weight gain of from 13.5 to 14.5%. A preferred polymer in the membrane coating dispersion comprises a quaternary polymethacrylate comprising a copolymer of ethyl acrylate and methyl methacrylate which contains trimethylammonium-methyl methacrylate in a range of about 1:40 relative to neutral monomers (neutral monomers are those monomers that do not have a quaternary ammonium group thereon). The drug delivery system of diltiazem hydrochloride may have the membrane coating contain a water soluble plasticizer in the range of 13.0% to 23.0% by weight of the coating, such as a membrane coating containing a water soluble plasticizer in the range of 15.0% to 21.0% based on the dry weight of a quaternary polymethacrylate membrane coating, and a water soluble surface active agent in the range from 0.100 to 0.300%, preferably 0.150 to 0.250% and, particularly 0.2% based on the dry weight of the total solids. The respective membrane coatings on the drug bead substrate of the medium release fraction (MRF) may, for example, comprise a weight gain of from 36 to 39%, and more particularly 37%. The membrane coating preferably contain a water soluble plasticizer in the range of 13.0% to 23.0%, preferably from 15.0% to 21.0% and, particularly 16.0%, based on the dry weight of the quaternary polymethacrylate. The membrane coating contain may also contain an anti-adherant silicone dioxide in the range of 3 to 7%, preferably from 4.0% to 6.0% and, particularly 5.0%, based on the dry weight of the quaternary polymethacrylate. The membrane coating on the drug bead substrate of the slow release fraction (SRF) may comprise a weight gain of from 45–52%, preferably 48–50% and, more particularly, 49%.

Figure 5:
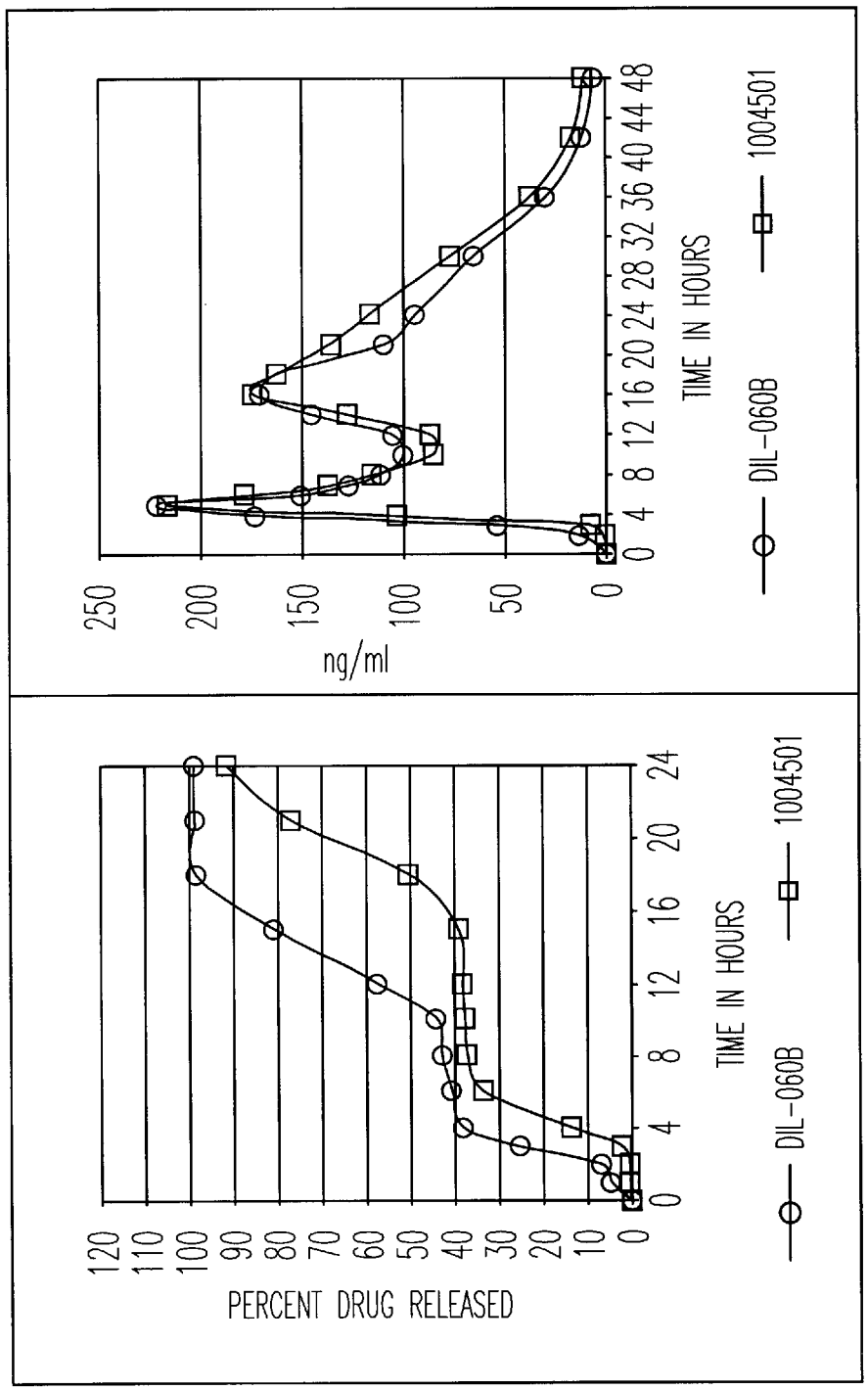
FIG. 5 shows inequivalent dissolution profiles of the Release system of the invention and Cardizem(® CD vs. bioequivalence for those two systems.

A fast release fraction of diltiazem HCl is prepared by forming multilayers of the deposited drug with a membrane coating dispersion on the drug bead substrate with a weight gain of from 10–20%, preferably 13–15% and, more particularly 14%. The percentages of ingredients, in a preferred embodiment of the membrane coating are 17.80% of quaternary polymethacrylate (QPM) (e.g., 14–28% by weight), 3.56% each (2.0–5.0% by weight) of triethyl citrate (TEC) and talc, respectively, 0.356% w/w of $SiO_2$ (e.g., 0.05 to 1% by weight), and 0.045% (e.g., 0.01 to 0.5% by weight) of simethicone emulsion and 0.039% w/w (e.g., 0.008–0.5% by weight)of sodium lauryl sulfate (SLS). Total solids are 25.36% w/w in water. The TEC/QPM ratio will range from 0.13 to 0.23, preferably from 0.15 to 0.21 and, particularly 0.20. The suggested range for SLS is from 0.0178 to 0.0534, preferably 0.0267 to 0.0445 and, particularly 0.0356%. In terms of solid/solid ratios with QPM as reference, the values are 20% TEC, 20% talc, 2% Silicone dioxide, and 0.2% SLS. After multilayering (e.g., at least two layers adding up to the desired weight of drug on the seed) of the drug suspension onto the bead or seed, and then application of a membrane coating dispersion, the membrane coated pellets are finish-coated with an Opadry®/Water dispersion, 10% w/w (Opadry® is the brand name for low viscosity (5 cps) hydroxypropyl methyl cellulose-based formulation traded by Colorcon® U.S.A). Low viscosity, in the practice of the present invention means less than 50 cps at STP. The pellets are then dried and subjected to heat treatment at from 45–50° C. for 24 hours to complete membrane formation by removing excessive moisture. The finish coat permits efficient drying without agglomeration. Agglomeration is attributed to tackiness that is the result of low glass transition temperature ($T_g$) of plasticized quaternary polymethacrylate. To perform within the practice of the present invention and to enable the system to display the necessary Bioequivalence Plasma profile of Cardizem® CD, the critical Fast Release Fraction must display a release profile of greater than 10% Total Drug Released in 3 hours and less than 40% Total Drug Released in 3 hours. This can be seen in the side-by-side profiles in FIG. 5. Note the extremely close Bioequivalence Profile for the two different materials, even with the significantly different release profiles for the same two systems (DIL-060B being the composition of the invention and 1004501 being Cardizem® CD).

A medium release fraction of diltiazem HCl is similarly prepared by forming a multilayer of a membrane coating dispersion on the drug bead substrate; however the weight gain is 37 to 43%, preferably 39 to 41% and, more particularly, 40%. The resulting medium release pellets are finish-coated and likewise subjected to heat treatment.

The slow release fraction of diltiazem HCl is also prepared by forming a multilayer membrane coating on the rug bead substrate, but with a weight gain of from 47–59%, preferably 51.5–53.5% and, more particularly, 52.5%. The slow release pellets are finish-coated and subjected to heat treatment.

The preferred MRF and SRF membranes are composed of 17.805% of quaternary polymethacrylate (QPM), 2.848% of triethyl citrate (TEC), 3.56% of talc, 0.889% of $SiO_2$, 0.045% of simethicone emulsion. Total solids are 25.15%. The TEC/QPM ratio will range from 0.13 to 0.23, preferably from 0.15 to 0.21 and, particularly 0.16. In terms of solid/solid ratios with QPM as reference, the values are 16% TEC, 20% talc, and 5% Silicone dioxide.

EXAMPLES OF THE PRESENT INVENTION

The preparation process and resulting product of the present invention are described in the following specific examples, which are intended to be merely illustrative, and the present invention is intended not to be limited thereto.

EXAMPLE I

| Preparation of Drug Bead Substrate | | | |
|---|---|---|---|
| Ingredient | Amount (g) | % w/w | Drug Beads |
| Purified water USP | 9.917 | 60.0 | Substrate Quality |
| Opadry ® Y5-7095 | 0.668 | 4.0 | |
| Diltiazem hydrochloride USP | 5.943 | 36.0 | |
| | 16.528 | 100.0 | |
| Purified water USP | 0.900 | 45.0 | |
| Opadry ® YS3-7065 | 0.200 | 10.0 | |
| Purified water USP | 0.900 | 45.0 | |
| | 2.000 | 100.0 | |
| Bowl change (30/35 mesh Nupareil ® white) | 1.700 | | 8.311 kg |

The drug layer dispersion is prepared by weighing Purified water into a tared container equipped with air mixer/propeller stirrer. With vigorous mixing, hydroxypropyl methylcellulose (Opadry® Y-5-7095) and Diltiazem hydrochloride USP are dispersed in water. The dispersion is mixed for 40 minutes until completely suspended; 30/35 mesh nonpareil seeds (Nu-pareil® White) are then dispensed into a polymeric bag-lined vessel.

The seeds are then charged into a Wurster film coater (GPCG-5, 7 inch (17.8 cm) Wurster HS by Gloat Air Techniques, Ramsey, N.J.).

The fluidization of nonpareils is started at an appropriate volume. The spraying of drug layer dispersion is started at an appropriate spray rate. Inlet temperature, air volume and spray rate are adjusted in order to layer drug dispersion effectively onto the seeds. When the dispersion is finished, a subcoat is applied. The subcoat is prepared by dispersing Hydroxypropyl methylcellulose (Opadry® US-307065) in Purified water. Total layering operation lasts more than four hours. Actual yield of layered beads is 99%; particle size analysis is as follows:

| Mesh | 14 | 16 | 18 | 20 | 30 | Pan | Total |
|---|---|---|---|---|---|---|---|
| Per cent retained | 1 | 2 | 94 | 3 | 0 | 0 | 100 |

EXAMPLE II
Preparation of Fast Release Fraction (FRF)
Quantities required for 14% weight gain

| Ingredients | Quantity (g) |
|---|---|
| Eudragit ® RS30D | 356.52 |
| Triethyl citrate NF | 21.39 |
| Silicone dioxide, NF (Syloid ® 244 FP) | 2.14 |
| Purified water, USP | 198.73 |
| Talc, USP (Alpha Fil 500) | 21.39 |
| Simethicone emulsion 30%, USP | 0.9 |
| Sodium lauryl sulphate | 0.30 |
|  | 6% solids |
| Diltiazem hydrochloride Drug Bead Substrate | 1000 |

Preparation of Fast Release Fraction (FRF)

A fast release fraction is produced by depositing multi-layers of a membrane coating dispersion on the drug bead substrate, using a water-insoluble, slightly permeable, non-enteric polymethacrylate compound such as RS (chemically, polyethylacrylate-methyl methacrylate trimethyl ammonium chloride) or poly (EA-MMA-TAMCL), which is available in a 1:2:0.1 ratio.

For preparation of the current invention, an RS 30D Membrane Coating Dispersion is prepared by screening Eudragit® RS 30D (30% w/w solids) through a U.S. standard 30 mesh screen into a tared vessel equipped with an air mixer. To the RS 30D is added the plasticizer, triethyl citrate (TEC), Sodium lauryl sulphate (surface active agent) and Silicone dioxide (Syloid(® 244 FP) as an antiadherant, which must be added to prevent agglomeration of RS 30D coated beads due to significant decrease in the glass transition temperature (T). In another tared container equipped with an air mixer, talc USP is added to Purified water. The separately prepared dispersions of RS 30D/TEC/Syloid/water and talc/water are mixed thoroughly.

First, the quantity of layered drug beads (calculated for FRF) is dispensed into the Wurster film coater (GPCG-5, 7 inch (17.8 cm) Wurster HS by Glatt). Using an appropriate air volume inlet temperature and spray rate, the designer applies the quantity of RS 30D membrane coating dispersion onto the drug-layered beads. When the RS 30d membrane coating dispersion onto the drug-layered beads. When the RS 30D membrane coating dispersion is depleted, sufficient Purified water is sprayed at a reduced rate, to clean the nozzle. The water is sprayed for five minutes while adjusting coating parameters for the subsequent Opadry® finish coat. The Opadry® dispersion (10% w/w) is sprayed onto membrane-coated beads at an appropriate spray rate, air volume and inlet temperature. When the Opadry® finish coat application is completed, the product (FRF) is dried at current parameters for five minutes, and then discharged and reconciled. Actual yield of the membrane-coated beads (FRF) is 99% and particle size analysis is as follows:

| Mesh | 14 | 16 | 18 | 20 | 30 | Pan | Total |
|---|---|---|---|---|---|---|---|
| Per cent retained | 1 | 43 | 55 | 1 | 0 | 0 | 100 |

EXAMPLE III
Preparation of Medium Release Fraction (MRF
Quantities required for 40% weight gain

| Ingredients | Quantity (g) |
|---|---|
| Eudragit ® RS30D | 1008.977 |
| Triethyl citrate NF | 48.427 |
| Silicone dioxide, NF (Syloid ® 244 FP) | 15.119 |
| Purified water, USP | 564.412 |
| Talc, USP (Alpha Fil 500) | 60.531 |
| Simethicone emulsion 30%, USP | 2.540 |
|  | (25.15% solids approx.) |
| Diltiazem hydrochloride Drug Bead Substrate | 1000.000 |

Preparation of Medium Release Fraction (MRF)

A quantity of layered drug beads (calculated for MRF) is dispensed into the Wurster film coater (GPCG-5, 7 inch (17.8 cm) Wurster HS by Glatt). Notice the absence of sodium lauryl sulfate in membrane coating dispersion and the lower ratio of triethyl citrate/RS 30D dry basis. The process employed for preparation of the FRF is repeated for the MRF. Actual yield of the membrane coated beads (MRF) is 98%; particle size analysis is as follows:

| Mesh | 14 | 16 | 18 | 20 | 30 | Pan | Total |
|---|---|---|---|---|---|---|---|
| Per cent retained |  | 68 | 31 | 1 | 0 | 0 | 100 |

EXAMPLE IV
Preparation of Slow Release Fraction (SRF)
Quantities required for 52.5% weight gain

| Ingredients | Quantity (g) |
|---|---|
| Eudragit ® RS30D | 1264.14 |
| Triethyl citrate NF | 60.67 |
| Silicone dioxide, NF (Syloid ® 244 FP) | 18.96 |
| Purified water, USP | 707.00 |
| Talc, USP (Alpha Fil 500) | 75.85 |
| Simethicone emulsion 30%, USP | 3.19 |
|  | 2129.80 g |
|  | (25.15% solids approx.) |
| Diltiazem hydrochloride Drug Bead Substrate | 1000.00 |

Preparation of Slow Release Fraction (SRF)

A quantity of layered drug beads (calculated for SRF) is dispensed into the Wurster film coater (GPCG-5 7 inch (17.8 cm) Wurster HS by Glatt). Notice the absence of sodium lauryl sulfate in the membrane coating dispersion dispersion and the lower ratio of triethyl citrate/RS 30D dry basis. The process employed for preparation of the FRF was repeated for the SRF. Actual yield of the membrane coated beads (SRF) is 98%; particle size analysis is as follows:

| Mesh | 14 | 16 | 18 | 20 | 30 | Pan | Total |
|---|---|---|---|---|---|---|---|
| Per cent retained | 1 | 94 | 5 | 0 | 0 | 0 | 100 |

EXAMPLE V
Curing of membrane-Coated Pellets

The fast, medium and slow release fractions are given heat treatment at 45–50° C. for 24 hours in a forced air oven, to complete the membrane formation process by removing excess moisture.

EXAMPLE VI

Drug Delivery System

In a triple filling process, the fast, medium and slow release fractions are filled in the same capsule, in a ratio of 37/26/37 based on potency. Furthermore, the desirable release profile will be obtained if the weight gain of individual fractions FRF, MRF and SRF are controlled within narrow limits, such as 13–15 (FRF), 39–41 (MRF) and 51.5–53.5 (SRF). A process flow diagram for the preparation of a Test batch or Bio Batch is presented on the following page. Two sub-batches are separately prepared until drug layering stage. These sub-batches are blended and then subdivided as shown in Column 2 of the following Table.

CALCULATIONS FOR A CAPSULE WITH A LABEL CLAIM OF 180 mg

| Name of fraction | Subdivision of drug layered pellets | Weight gain, % | Theoretical potency of membrane coated pellets based on potency of uncoated pellets, % | Fill weight, mg |
|---|---|---|---|---|
| FRF | 37.0 | 14 | 61.40 | 108.47 |
| MRF | 26.0 | 40 | 50.00 | 93.60 |
| SRF | 37.0 | 52.5 | 45.90 | 145.10 |
| TOTAL | 100.0 | | | 347.17 |

DILTIAZEM ER CAPSULES (120/180/240/300 mg)
<u>Scheme For Test Batch</u>
Mfg. Equipment : GPCG – 120  18" Wurster HS.
PROCESS FLOW DIAGRAM
In-Process Evaluation :
① Drug Layer Dispersion
② Drug Layered Pellets
③ Blending
④ Fractions
⑤ Encapsulation
⑥ Finished Product Analysis
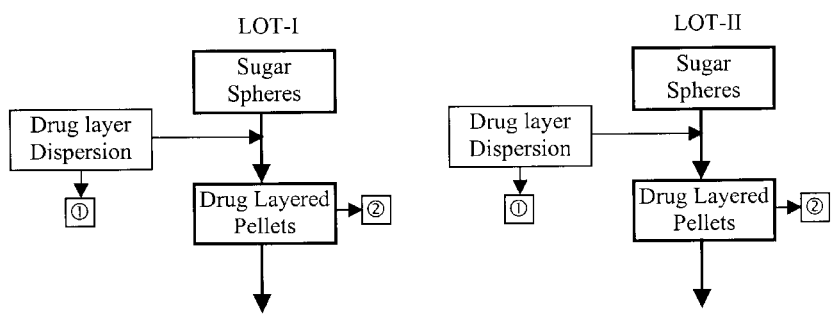

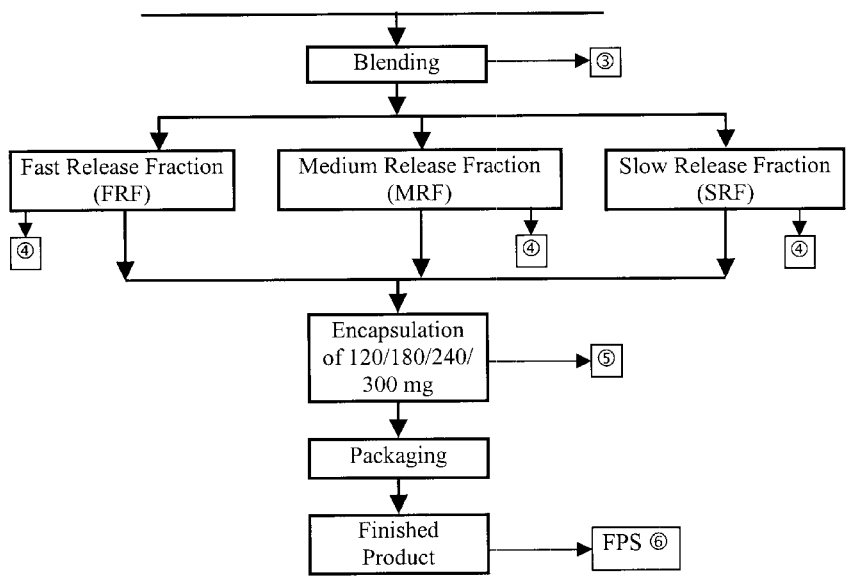

UNIT COMPOSITION OF FINAL FORMULA

| Ingredients | 120 mg | 180 mg | 240 mg | 300 mg |
|---|---|---|---|---|
| Diltiazem Hydrochloride, USP | 120.00 | 180.00 | 240.00 | 300.00 |
| Opadry ® Clear Y-5-7095 | 13.484 | 20.226 | 26.968 | 33.71 |
| Opadry ® Clear YS-3-7065 | 6.332 | 9.498 | 12.664 | 15.83 |
| SugarSpheres, NF (30/35 mesh Nu-pareils ®) | 33.488 | 50.232 | 66.976 | 83.72 |
| Eudragit ® RS 30D Ph. Eur. | 41.764 | 62.646 | 83.528 | 104.41 |
| Silicone Dioxide, NF (Syloid ® 244FP) | 1.90 | 2.85 | 3.80 | 4.75 |
| Triethyl Citrate PG/NF | 6.924 | 10.386 | 13.848 | 17.31 |
| Alpha Fil 500 Talc, USP | 8.348 | 12.522 | 16.696 | 20.87 |
| Simethicone Emulsion 30%, USP (Dow Corning ® 7-9245) | 0.104 | 0.156 | 0.208 | 0.26 |
| Sodium Lauryl Sulphate | 0.016 | 0.024 | 0.032 | 0.04 |
| TOTAL | 232.36 | 348.54 | 464.72 | 580.90 |

EXAMPLE VII

| Raw Material | Mg/capsule | % (w/w) | Batch quantities (20,000 capsules) kg |
|---|---|---|---|
| Diltiazem hydrochloride, USP | 300.00 | 51.644 | 6.0000 |
| Opadry ® Clear Y-5-7095 | 33.71 | 5.803 | 0.6742 |
| Opadry ® Clear YS-3-7065 | 15.83 | 2.725 | 0.3166 |
| Sugar Spheres, NF (30/35 mesh Nu-pareils ®) | 83.72 | 14.412 | 1.6744 |
| Eudragit ® RS30D Ph. Eur. | 104.41 | 17.973 | 2.0882 |
| Silicone dioxide, NF (Syloid ® 244 FP) | 4.75 | 0.817 | 0.0950 |
| Triethyl citrate PG/NF | 17.31 | 2.979 | 0.3462 |
| Alpha Fil 500 Talc, USP | 20.87 | 3.592 | 0.4174 |
| Simethicone emulsion 30%, USP (Dow Corning ® 7.9245) | 0.26 | 0.044 | 0.0052 |
| Sodium Lauryl Sulphate | 0.04 | 0.006 | 0.0008 |
| TOTAL | 580.90 | 99.995 | 11.6000 |

In order to prepare a batch of 20,000 capsules, a 4% w/w dispersion of Hydroxypropyl methylcellulose (HPMC) was prepared in water using a Lightning Mixer (equipped with an impeller). Then, 6.0 kg of Diltiazem hydrochloride was slowly suspended in the HPMC dispersion. The preparation of the dispersions was mixing these ingredients at a controlled RPM.

Then the HPMC/Diltiazem hydrochloride dispersion was pumped through a calibrated, peristaltic pump to deliver the HPMC/Diltiazem hydrochloride dispersion to fluidized Nu-Pareil® White core substrate at an appropriate air volume. The HPMC/Diltiazem hydrochloride dispersion was sprayed at an appropriate spray rate. The inlet air temperature, air volume, and spray rate were adjusted to effectively layer the entire HPMC/Diltiazem hydrochloride dispersion on to Nu-Pareil® White core substrate. Then a sub-coat of a proprietary HPMC (Opadry® YS-3-7065) was applied to layered drug beads in order to theoretically, provide a weight gain of one percent, using fluidized film coating equipment.

BIOAVAILABILITY STUDIES

A randomized, 2 treatment, 2 period, single dose, crossover comparative bioavailability study of Diltiazem Hydrochloride Extended Release Capsules, 180 mg Manufactured by Wockhardt Limited and Cardizem® CD manufactured by Hoechst Marion Roussel was conducted in 18 healthy male volunteers, 18–45 years of age, under fasted protocol. Single oral dose of 180 mg was administered with 240 ml water. Blood samples were collected in Vacutainers® containing heparin before dosing (2×5 ml) and the following times after capsule administration: 2,3,4,5,6,7,8,10,12,14,16,18,21,24, 30,36,42, and 48 hours. Subjects fasted overnight before dosing and for at least four hours thereafter. Water was not permitted for 1 hour before and 1 hour after dosing, but was allowed at all other times. Standard meals were provided at about 4 and 9 hours after capsule administration. Washout period is one week.

A sensitive analytical method for the analysis of Diltiazem Hydrochloride is developed within the Wockhardt R & D Center. Data analysis included determination of ratios and confidence intervals of the parameters of bioequivalence.

PARAMETER OF BIOEQUIVALENCE

| | DIL-060B | |
|---|---|---|
| Parameter | RATIO (T/R) | C.I. |
| $C_{max}$ | 0.96 | 86.67–105.45 |
| $AUC_{0-t}$ | 0.94 | 83.09–104.15 |
| $AUC_{0-\infty}$ | 1.08 | 100.08–115.96 |
| $LN_{cmax}$ | 0.99 | 84.76–104.63 |
| $LNAUC_{0-t}$ | 0.99 | 82.32–103.51 |
| $LNAUC_{0-\infty}$ | 1.01 | 99.95–115.07 |

A comparison of the release profiles for the system of U.S. Pat. No. 5,968,522 and that of the present invention is also informative with respect to showing substantive differences therebetween. The activities for the fractions are for the pellets of the U.S. Pat. No. 5.968,552.

| Hours | Fast Rel. F. | Int. Rel. F. | Slow Rel. F. | Patent '552 | Invention |
|---|---|---|---|---|---|
| 3 | ≧40% | | | | |
| 6 | | ≦30% | ≦20% | 20–45% | 20–45% |
| 12 | | ≧35% | ≦35% | 20–50% | 55–70% |
| 18 | | | | 35–70% | 75–100% |
| 24 | | | ≧50% | ≧70% | |
| 30 | | | | ≧85% | |

As can be seen from this data, the release profiles at 12 and 24 hours are dramatically different and non-equivalent for the invention and the material of U.S. Pat. No. 5,968,552. This difference is important, as the release profile of the invention produces a bioequivalent plasma profile, and the composition of the Patent is therefore not likely to produce such a bioequivalence plasma profile. Another desirable range within the practice of the invention is for the system to release from 57–70% (or 58–68%) at 12 hours and for the system to have release between 78–100% (or 80–100%) at 18 hours. Another measure of the success of the system of the present invention is that the graphing of the Bioequivalence in Plasma versus Time shown in FIG. 5 demonstrates that the profile of the invention, between 4–20 hours after delivery, does not deviate from the profile of Cardizem® CD at any time by more than 25 ng/ml (nanograms per milliliter). The standard deviation from the profile of Cardizem(® CD over the range of 4–30 hours is less than 10 ng/ml, and less than 8%.

What is claimed is:

1. A once-a-day controlled release drug delivery system of diltiazem hydrochloride comprising a blend of three pellet fractions:

a) a fast release fraction (FRF) of diltiazem HCl having multiple layers of diltiazem HCl particles on a drug bead substrate and a membrane coating dispersion comprising an anionic surface-active agent, over said multiple layers, the fast release fraction providing a profile of drug release of greater than 10% Total Drug Released in 3 hours and less than 40% Total Drug Released in 3 hours;

b) a medium release fraction (MRF) of diltiazem HCl having multiple layers of diltiazem HCl particles on a drug bead substrate and a membrane coating dispersion over said multiple layers; and c) a slow release fraction (SRF) of diltiazem HCl having multiple layers of diltiazem HCl particles on a drug bead substrate and a membrane coating dispersion over said multiple layers; wherein the blend exhibits a cumulative in-vitro drug release profile, when tested in the USP Dissolution Apparatus, Type II, in 0.1N HCl maintained at 37° C., using 100 RPM, as follows:

d) 20–40% released in 6 hours e) 55–70% released in 12 hours, and f) more than 75% released in 18 hours.

2. The drug delivery system of claim 1 wherein the pellets comprise beads having diltiazem hydrochloride deposited as multilayers in low viscosity hydroxypropyl methyl cellulose having a viscosity of less than 50 cps.

3. The drug delivery system of claim 1 wherein the diltiazem hydrochloride is applied as three multilayers; and the weight percentages of diltiazem hydrochloride are 35–43% FRF/24–32% MRF/28–40% SRF.

4. The drug delivery system of claim 1 wherein the weight percentages of diltiazem hydrochloride are 37–43% FRF/26–31.5% MRF/28.5–37% SRF.

5. The drug delivery system of claim 1 wherein said membrane coating on the KKX fast release pellets comprises a weight gain of from 10–20%.

6. The drug delivery system of claim 1 wherein said membrane coating on the fast release pellets comprises a weight gain of 12–15%.

7. The drug delivery system of claim 1 wherein said membrane coating on the fast release pellets comprises a weight gain of from 12.5 to 13.5%.

8. The drug delivery system of claim 2 wherein said membrane coating comprises a quaternary polymethacrylate polymer dispersion comprising a copolymer of ethyl acrylate and methyl methacrylate comprising trimethylammoniummethyl methacrylate in a range of about 1:40 relative to the neutral monomers.

9. The drug delivery system of claim 3 wherein said membrane coating comprises a water soluble plasticizer in the range of 13.0% to 23.0%.

10. The drug delivery system of claim 3 wherein said membrane coating comprises a water soluble plasticizer in the range of 15.0% to 21.0%.

11. The drug delivery system of claim 3 wherein said membrane coating comprises a water soluble surface active agent in the range from 0.100 to 0.300% based on the dry weight of the quaternary polymethacrylate.

12. The drug delivery system of claim 1 wherein said membrane coating on the medium release pellets comprises a weight gain of from 33 to 45%.

13. The drug delivery system of claim 6 wherein said membrane coating comprises a quaternary polymethacrylate dispersion comprising a copolymer of ethyl acrylate and methyl methacrylate comprising trimethylammoniummethyl methacrylate in a range of about 1:40 relative to the neutral monomers.

14. The drug delivery system of claim 7 wherein said membrane coating comprises a water soluble plasticizer in the range of 13.0% to 23.0%, based on the dry weight of the quaternary polymethacrylate.

15. The drug delivery system of claim 7 wherein said membrane coating comprises an antiadherant silicone dioxide in the range of 2 to 5%, based on the dry weight of the quaternary polymethacrylate.

16. The drug delivery system of claim 1 wherein said membrane coating on the slow release pellets comprises a weight gain of from 45–52%.

17. The drug delivery system of claim 10 wherein said membrane coating comprises a quaternary polymethacrylate dispersion comprising a copolymer of ethyl acrylate and methyl methacrylate comprising trimethylammoniummethyl methacrylate in a range of about 1:40 relative to the neutral monomers.

18. The drug delivery system of claim 12 wherein said membrane coating comprises a water soluble plasticizer in the range of 13.0% to 23.0%, based on the dry weight of the quaternary polymethacrylate.

19. The drug delivery system of claim 12 wherein said membrane coating comprises an antiadherant silicone dioxide in the range of 3 to 7%, based on the dry weight of the quaternary polymethacrylate.

20. The drug delivery system of claim 1 wherein the amount of anionic surface-active agent is from 0.100 to 0.300%.

21. The drug delivery system of claim 1 wherein said anionic surface-active agent sodium lauryl sulfate.

* * * * *

UNITED STATES PATENT AND TRADEMARK OFFICE
CERTIFICATE OF CORRECTION

PATENT NO. : 6,635,277 B2
DATED : October 21, 2003
INVENTOR(S) : Javed Hussain, Habil F. Khorakiwala and Vinay K. Sharma It is certified that error appears in the above-identified patent and that said Letters Patent is hereby corrected as shown below:

Title page,
Item [56], References Cited, OTHER PUBLICATIONS, delete "505-512" and insert -- 507-512 -- therefor.
U.S. PATENT DOCUMENTS, delete "Deboeck et al." and insert -- Eichel et al. -- therefor.

Column 1,
Line 9, delete "filed" before "Apr. 12".

Column 3,
Line 21, delete "67x0-10%" and insert -- 67% x 0-10% -- therefor.

Column 4,
Line 26, delete """ before "Chemistry" and insert -- " -- therefor.
Line 62, delete ")" after "796".
Line 62, delete "91997)" and insert -- (1997) -- therefor.

Column 5,
Line 4, delete "antiaderants" and insert -- antiadherants -- therefor.

Column 6,
Line 61, delete "Cardizem(®" and insert -- Cardizem® -- therefor.

Column 7,
Line 31, delete "Cardizem(®" and insert -- Cardizem® -- therefor.

Column 9,
Line 5, delete "contain" after "coating".
Line 43, delete "C." and insert -- C -- therefor.
Line 66, delete "rug" and insert -- drug -- therefor.

Column 10,
Line 48, delete "Gloat" and insert -- Glatt -- therefor.

Column 11,
Line 47, delete "30d" and insert -- 30D -- therefor.

Column 12,
Line 2, insert -- ) -- after "(MRF".
Line 48, delete "GPCG-5 7" and insert -- GPCG-5, 7 -- therefor.
Line 50, delete "dispersion" after "coating".

UNITED STATES PATENT AND TRADEMARK OFFICE
CERTIFICATE OF CORRECTION

PATENT NO. : 6,635,277 B2
DATED : October 21, 2003
INVENTOR(S) : Javed Hussain, Habil F. Khorakiwala and Vinay K. Sharma It is certified that error appears in the above-identified patent and that said Letters Patent is hereby corrected as shown below:

<u>Column 21,</u>
Line 24, delete "C." and insert -- C -- therefor.
Line 40, delete "KKX" after "the".

<u>Column 22,</u>
Line 51, insert -- is -- after "agent".

Signed and Sealed this

Third Day of February, 2004

JON W. DUDAS
*Acting Director of the United States Patent and Trademark Office*